US006753138B1

(12) United States Patent
Schneider et al.

(10) Patent No.: US 6,753,138 B1
(45) Date of Patent: Jun. 22, 2004

(54) USE OF PROTHYMOSIN IN THE DIAGNOSIS AND TREATMENT OF ENDOMETRIOSIS

(75) Inventors: Patrick A. Schneider, Temecula, CA (US); Cynthia K. French, Irvine, CA (US); Karen K. Yamamoto, San Clemente, CA (US)

(73) Assignee: Reprogen, Inc., Irvine, CA (US)

( * ) Notice: Subject to any disclaimer, the term of this patent is extended or adjusted under 35 U.S.C. 154(b) by 0 days.

(21) Appl. No.: 09/485,193

(22) PCT Filed: Jun. 3, 1999

(86) PCT No.: PCT/US99/12336

§ 371 (c)(1),
(2), (4) Date: Dec. 27, 2000

(87) PCT Pub. No.: WO99/63116

PCT Pub. Date: Dec. 9, 1999

Related U.S. Application Data

(60) Provisional application No. 60/088,016, filed on Jun. 4, 1998.

(51) Int. Cl.[7] .......................... C12Q 1/68; C12P 19/34; G01N 33/53; C07H 21/04; C07H 21/02

(52) U.S. Cl. .......................... 435/6; 435/7.1; 435/7.21; 435/7.92; 435/7.93; 435/7.94; 435/40.5; 435/40.51; 435/40.52; 435/91.1; 435/91.2; 536/23.1; 536/24.3; 536/24.31; 536/24.33

(58) Field of Search .......................... 435/6, 7.1, 91.2, 435/7.21, 40.5, 40.51, 40.52, 7.92, 7.93, 7.94, 91.1; 530/350; 536/23.1, 24.3, 24.33, 24.31

(56) References Cited

U.S. PATENT DOCUMENTS 4,696,915 A 9/1987 Horecker .................... 514/21
5,248,591 A 9/1993 Puente ...................... 435/7.1

FOREIGN PATENT DOCUMENTS

WO WO 95/32708 12/1995
WO WO 98/42185 1/1998
WO WO 98/12324 3/1998

OTHER PUBLICATIONS

Baxevanis, Constantin N. et al., "Prothymosin α Enhances Human and Murine MHC Class II Surface Antigen Expression and Messenger RNA Accumulation," 148(7):1979–1984 (1992).

Hill, Joseph A., MD, "Immunology and Endometriosis," *Obstetrics and Gynecology Clinics of North America* 24(2):291–306 (1997).

Ota and Igarashi, "Expression of major histocompatibility complex class II antigen in endometriotic tissue in patients with endometriosis and adenomyosis," *Fertility and Sterility* 60(5):834–838 (1993).

Oikawa, Mamoru et al., "Expression of Gonadotropin–Releasing Hormone and Prothymosin–α Messenger Ribonucleic Acid in the Ovary," *Endocrinology* 127(5):2350–2356 (1990).

Ota, H. et al., "Is adenomyosis an immune disease?," *Hum Reprod Update* 4(4):360–7 (1998) Abstract only.

Sharpe–Timms, Kathy L., PhD, HCLD, "Basic Research in Endometriosis," *Obstetrics and Cynecology Clinics of North America* 24(2):269–290 (1997).

Bruner et al. "Suppression of matrix metalloproteinases inhibits establishment of ectopic lesions by human endometrium in nude mice," J. Clin. Invest 99:2851–2857 (1997).

Giudice et al. "Status of current research on endometriosis," J Reprod Med 43:252–262 (1998).

*Primary Examiner*—S. Zitomer
(74) *Attorney, Agent, or Firm*—Townsend and Townsend and Crew LLP

(57) ABSTRACT

Prothymosin expression is up-regulated in endometriotic tissue. This invention provides methods of diagnosing endometriosis by detecting up-regulation of a prothymosin gene product, and methods of treating endometriosis by down-regulating expression of prothymosin in ectopic or eutopic endometriotic tissue.

32 Claims, No Drawings

USE OF PROTHYMOSIN IN THE DIAGNOSIS AND TREATMENT OF ENDOMETRIOSIS

CROSS-REFERENCE TO RELATED APPLICATION

This application is filed as a §371 of International patent application no. PCT/US99/12336, filed Jun. 3, 1999, and claims the benefit of U.S. provisional patent application serial No. 60/088,016, filed Jun. 4, 1998. This application is related to, but does not claim priority on, U.S. patent application Ser. No. 09/047,910, filed Mar. 25, 1998 (J. Boyd et al.) now U.S. Pat. No. 6,429,353.

FEDERALLY SPONSORED RESEARCH OR DEVELOPMENT

Not applicable.

BACKGROUND OF THE INVENTION

This invention is directed to the field of medical diagnostics and treatment. More particularly, it is directed to methods of diagnosing and treating endometriosis based on the pathologic up-regulation of prothymosin in endometriotic tissue.

Endometriosis is a painful disorder that is characterized by the ectopic implantation of functioning endometrial tissue into the abdominal wall and the outer surface of various organs including, most commonly, the lower bowel, ovaries and fallopian tubes. P. Vigano et al. (1991) *Fertility and Sterility* 56:894. Currently, endometriosis-specific genes have not been identified and the events relating to the development of endometriosis are poorly understood. However, several reports suggest that retrograde menstruation linked with abnormal immune function may play a role in establishing ectopic endometriotic lesions. T. Ishimaru and H. Masuzaki (1991) *Am. J. Obstet. Gynecol.* 165:210–214. The identification of genes that are differentially expressed in endometriotic lesions compared to healthy endometrial tissue would provide markers for diagnosing endometriosis and targets for therapeutic intervention in endometriosis.

SUMMARY OF THE INVENTION

Human endometrial tissue cultured in mice grows and mimics the progression to endometriosis. We have discovered that prothymosin expression is up-regulated in such tissue. This invention provides methods and materials that take advantage of this fact. More particularly, this invention provides methods of diagnosing endometriosis by detecting up-regulation of prothymosin in a sample from a patient suspected of having endometriosis. The methods involve detecting increased amounts of prothymosin mRNA or prothymosin protein in the sample compared to normal. This invention also provides methods of treating endometriosis by down-regulating the level of prothymosin activity in ectopic or eutopic endometrial tissue. These methods include decreasing transcription, processing or translation of prothymosin mRNA, as well as inhibiting biological activity of prothymosin.

In one aspect this invention provides a method for use in the diagnosis of endometriosis in a subject. The method comprises the steps of: detecting a test amount of a prothymosin gene product in a sample from the subject; and comparing the test amount with a normal amount of the prothymosin gene product in a control sample. A test amount above the normal amount provides a positive indication in the diagnosis of endometriosis. In one aspect, the method comprises ectopic endometrial tissue, eutopic endometrial tissue, peritoneal fluid, blood, vaginal secretion or urine.

In one embodiment of the method, the prothymosin gene product is prothymosin mRNA or cDNA. The step of detecting can comprise the steps of contacting the prothymosin mRNA or cDNA with a polynucleotide of at least 7 to about 50 nucleotides in length that specifically hybridizes to the prothymosin mRNA or cDNA and detecting hybridization between the polynucleotide and the mRNA or cDNA. In one embodiment, the polynucleotide is a primer and the step of detecting hybridization comprises initiating reverse transcription of prothymosin mRNA with the primer, and detecting a prothymosin mRNA reverse transcript. Detection of the reverse transcript indicates that the polynucleotide has specifically hybridized to prothymosin mRNA. In another embodiment the prothymosin mRNA or cDNA is immobilized and the step of contacting comprises contacting the immobilized mRNA or cDNA with the polynucleotide. In another embodiment the polynucleotide is immobilized and the step of contacting comprises contacting the immobilized polynucleotide with the prothymosin mRNA or cDNA. In another embodiment the biological sample is a fixed tissue sample and the step of contacting comprises contacting the polynucleotide with the mRNA or cDNA in situ on the fixed tissue sample.

In another embodiment the step of detecting comprises the steps of amplifying the prothymosin mRNA or cDNA to produce an amplification product and detecting the amplification product. In one method, the step of detecting the amplification product comprises contacting the amplification product with a polynucleotide of at least 7 to about 50 nucleotides in length that specifically hybridizes to the amplification product, and detecting hybridization between the polynucleotide and the amplification product. In another method, the step of detecting the amplification product comprises determining the nucleotide sequence of the amplification product. In another method, the step of detecting the amplification product comprises determining the mass of the amplification product.

In another embodiment, the prothymosin gene product is prothymosin polypeptide. In one method, the step of detecting comprises detecting binding prothymosin polypeptide by immunoassay. The immunoassay can be non-competitive or competitive.

A competitive immunoassay comprises detecting binding between the prothymosin polypeptide and an antibody comprising a detectable moiety, e.g., selected from the group consisting of a fluorescent label, a radioactive label, an enzymatic label, a biotinyl group, or an epitope recognized by a secondary reporter. A non-competitive immunoassay comprises the steps of capturing the prothymosin polypeptide from the sample on a solid phase with a first antibody specific for prothymosin polypeptide; and detecting capture of the prothymosin polypeptide by contacting the solid phase with a second antibody specific for prothymosin polypeptide and detecting binding between the second antibody and prothymosin polypeptide. Another non-competitive immunoassay comprises the steps of binding the prothymosin polypeptide from the sample to a solid phase; and detecting the prothymosin polypeptide by contacting the solid phase with an antibody specific for prothymosin polypeptide and detecting binding between the antibody and prothymosin polypeptide.

In another embodiment the method involves detecting the polypeptide by contacting the sample with an affinity agent that binds to prothymosin polypeptide and detecting binding between the affinity agent and the prothymosin polypeptide. In another method, the step of detecting comprises detecting an analyte in the sample having the mass of prothymosin polypeptide.

In another aspect this invention provides method for use in the monitoring the progress of endometriosis in a subject comprising the steps of detecting a first test amount of a prothymosin gene product in a sample from the subject at a first time; detecting a second test amount of the prothymosin gene product in a sample from the subject at a second, later time; and comparing the first test amount with the second test amount. An increase in the amount between the first time and the second time indicates progression of endometriosis and a decrease in the amount between the first time and the second time indicates remission of endometriosis.

In another aspect this invention provides a kit comprising a compound that binds a prothymosin gene product and instructions to (1) use the compound for detecting prothymosin in a patient sample, and (2) to diagnose endometriosis based on an elevated amount of the prothymosin gene product in the sample compared with a normal amount of prothymosin.

In another aspect this invention provides method for use in the diagnosis of endometriosis in a subject comprising detecting a prothymosin gene product in endometrial tissue from the subject in vivo, whereby detection of the gene product provides a positive indication in the diagnosis of endometriosis. In one embodiment the method comprises administering to the subject a compound that specifically binds to a prothymosin gene product and detecting binding between the compound and the prothymosin gene product. In one embodiment of the method the compound comprises a gamma-emitting or positron-emitting radioisotope and binding is detected by detecting the radioisotope by camera imaging or Geiger counter. In another embodiment of the method the compound comprises a paramagnetic isotope and binding is detected by detecting the paramagnetic isotope by magnetic resonance imaging ("MRI").

In another aspect this invention provides method for the treatment of endometriosis in a subject comprising administering to the subject a probe comprising a detectable label and a ligand that specifically binds a prothymosin gene product, to allow binding between the probe and the prothymosin gene product; identifying an endometriotic lesion in situ by locating bound label; and excising the endometriotic lesion. In one embodiment this method comprises administering the probe into the peritoneum of the subject, wherein the probe comprises an antibody ligand that specifically binds prothymosin and a radioactive label; identifying an endometriotic lesion in situ by locating bound probe with a Geiger counter; and excising the endometriotic lesion laparoscopically.

In another aspect this invention provides a screening method for determining whether a compound modulates the expression of a prothymosin gene product in an endometrial cell comprising the steps of contacting the cell with the compound; and determining whether expression of the prothymosin gene product is different that expression in a control cell which has not been contacted with the compound. A difference between expression in the endometrial cell and the control cell indicates that the agent modulates expression of the prothymosin gene product. In one aspect of this method the endometrial cell is comprised within endometriotic tissue cultured as a xenograft in a mouse; the step of contacting comprises administering the compound to the mouse; and the step of determining comprises in vitro determination of expression of the gene product after removing the tissue from the mouse.

In another aspect this invention provides a method for the treatment of endometriosis in a subject comprising the step of administering to the subject a compound that decreases prothymosin activity in eutopic endometrial tissue or ectopic endometrial tissue in the subject. The compound can inhibit expression of prothymosin mRNA or the activity of prothymosin protein. In one aspect the inhibitory polynucleotide is a polynucleotide comprising an antisense sequence of at least 7 nucleotides that specifically hybridizes to a nucleotide sequence within prothymosin mRNA, whereby the polynucleotide inhibits the activity of the prothymosin mRNA. In another aspect the inhibitory polynucleotide is a ribozyme that cleaves prothymosin mRNA. In another aspect the endometrial cells are transfected with an expression vector comprising expression control sequences operatively linked to a nucleotide sequence encoding the antisense polynucleotide, whereby the vector expresses the polynucleotide.

DETAILED DESCRIPTION OF THE INVENTION

I. Definitions

Unless defmed otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

"Polynucleotide" refers to a polymer composed of nucleotide units. The nucleotide units may be naturally occuring or non-naturally occuring. Naturally occuring nucleotides include ribonucleotides ("RNA") and deoxyribonucleotides ("DNA"). Non-naturally occuring nucleotides include nucleotide analogs that comprise non-naturally occuring bases or that engage in linkages with other nucleotides other than the naturally occuring phosphodiester bond. Thus, nucleotide analogs include, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defmed sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence. encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing "antisignals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defmed ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2X SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2×(or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Affinity agent" refers to any material capable of adsorbing an analyte. This includes, without limitation, anion exchange materials, metal chelators, antibodies, protein ligands and polynucleotides.

A "ligand" is a compound that specifically binds to a target molecule.

A "receptor" is compound that specifically binds to a ligand.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and $F(ab)'_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

A ligand or a receptor (e.g., an antibody) "specifically binds to" or "is specifically immunoreactive with" a compound analyte when the ligand or receptor functions in a binding reaction which is determinative of the presence of the analyte in a sample of heterogeneous compounds. Thus, under designated assay (e.g., immunoassay) conditions, the ligand or receptor binds preferentially to a particular analyte and does not bind in a significant amount to other compounds present in the sample. For example, a polynucleotide specifically binds under hybridization conditions to an analyte polynucleotide comprising a complementary sequence; an antibody specifically binds under immunoassay conditions to an antigen analyte bearing an epitope against which the antibody was raised; and an adsorbent specifically binds to an analyte under proper elution conditions.

"Immunoassay" refers to a method of detecting an analyte in a sample involving contacting the sample with an antibody that specifically binds to the analyte and detecting binding between the antibody and the analyte. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., PD. Fahrlander and A. Klausner, *Bio/Technology* (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic ammes.

"Small molecule" refers to organic or inorganic molecules up to about 5000 Da, up to about 2000 Da, or up to about 1000 Da. The term excludes organic biopolymers (e.g., proteins, nucleic acids, etc.).

A "subject" of diagnosis or treatment is a human or non-human mammal.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Prognostic" means predicting the probable development (e.g., severity) of a pathologic condition.

"Test amount" refers to an amount of an analyte in a subject sample, which is then compared to a normal amount of the analyte in a sample (e.g., from a healthy individual) such that the relative comparison of the values provides a reference value for diagnosing a designated disease. Depending upon the method of detection, the test amount may be a determination of the amount of the analyte, but it is not necessarily an amount. The test amount may also be a relative value, such as a plus or a minus score, and also includes an amount indicating the presence or absence of the analyte in a sample.

"Normal amount" refers to an amount or a range of an analyte in a biological sample that indicates health or lack of pathology.

"Diagnostic amount" refers to an amount of an analyte in a subject sample that is consistent with a particular diagnosis for a designated disease.

"Prognostic amount" refers to an amount or range of an analyte in a subject sample that is consistent with a particular prognosis for a designated disease.

"Plurality" means at least two.

"Graft" refers to any free (unattached) cell, tissue or organ for transplantation.

"Xenograft" refers to a transplanted cell, tissue or organ derived from an animal of a different species.

II. Up-Regulation of Prothymosin as a Marker for Endometriosis

We have discovered that prothymosin is up-regulated in human endometrial tissue cultured in a mouse model of endometriosis. This discovery enables methods of diagnosing endometriosis by detecting an increase in prothymosin expression and methods of treating endometriosis by down-regulating prothymosin activity. The experiments by which we made this discovery are described in detail in the Examples. However, we summarize those experiments here.

Severe Combined Immunodeficient (SCID) mice were used as hosts for normal human endometrial tissue. The mice do not reject these xenografts. In growth, the tissue mimics tissue lesions in endometriosis. This method is described in more detail in co-pending U.S. patent application Ser. No. 09/047,910, filed Mar. 25, 1998 (J. Boyd et al.).

We prepared a subtracted library using the cDNA from the xenograft tissue as a tester and normal human endometrial cDNA and normal mouse cDNA as a driver. We used the subtracted probe to screen an endometrial carcinoma library. From this screening we identified a clone, referred to as "REPRO-EN-203." Based on its sequence, we determined that REPRO-EN-203 encoded prothymosin.

Prothymosin is a highly acidic precursor protein of thymosin. Prothymosin is a nuclear protein involved in normal cell proliferation and has immunoregulatory effects on various cell types including natural killer cells and T cells. Prothymosin stimulates NK and lymphokine-activated killer cells by enhancing the expression of IL-2 and IL-1 receptors. In addition, prothymosin acts as an accessory signal for the adhesion of IL-2-activated lymphocytes to endothelial cells via the lymphocyte function-associated antigen-1 (LFA-1) family of integrin adhesion molecules. It is interesting to note that ICAM-1, the ligand for LFA-1, is expressed at high levels in endometrial stromal cells from normal subjects, but is shed in endometriosis patients, which may result in reduced immunodetection of ectopic endometrial tissue.

"Prothymosin" refers to a protein that stimulates cell proliferation and that has an amino acid sequence substantially identical to the amino acid sequence presented herein. This includes allelic variants of prothymosin. The mass of prothymosin polypeptide is about 12 kD. The size of prothymosin mRNA is about 1.2 kb. The nucleotide sequence (SEQ ID NO: 1) and deduced amino acid sequence (SEQ ID NO:2) of clone REPRO-EN-203 is presented in Table 1. We also compared the sequence of REPRO-EN-203 with a sequence for prothymosin from GenBank. The sequences were identical in the coding region and virtually identical in the non-coding regions.

TABLE 1

| | | |
|---|---|---|
| 1 | GAAAAGCCATCTTTGCATTGTTCCTCATCCGCCTCCTTGCTCGCCGCAGC | 50 |
| 51 | CGCCTCCGCCGCGCGCCTCCTCCGCCGCCGCGGACTC&GGCAGCTTTATC | 100 |
| 101 | GCCAGAGTCCCTGAACTCTCGCTTTCTTTTTAATCCCCTGCATCGGATCA | 150 |
| 151 | CCGGCGTGCCCCACCATGTCAGACGCAGCCGTAGACACCAGCTCCGAAAT<br>METSerAspAlaAlaValAspThrSerSerGluIl | 200 |
| 201 | CACCACCAAGGACTTAAAGGAGAAGAAGGAAGTTGTGGAAGAGGCAGAAA<br>eThrThrLysAspLeuLysGluLysLysGluValValGluGluAlaGluA | 250 |
| 251 | ATGGAAGAGACGCCCCTGCTAACGGGAATGCTAATGAGGAAAATGGGGAG<br>snGlyArgAspAlaProAlaAsnGlyAsnAlaAsnGluGluAsnGlyGlu | 300 |
| 301 | CAGGAGGCTGACAATGAGGTAGACGAAGAAGAGGAAGAAGGTGGGGAGGA<br>GlnGluAlaAspAsnGluValAspGluGluGluGluGluGlyGlyGluGl | 350 |
| 351 | AGAGGAGGAGGAAGAAGAAGGTGATGGTGAGGAAGAGGATGGAGATGAAG<br>uGluGluGluGluGluGluGlyAspGlyGluGluGluAspGlyAspGluA | 400 |
| 401 | ATGAGGAAGCTGAGTCAGCTACGGGCAAGCGGGCAGCTGAAGATGATGAG<br>spGluGluAlaGluSerAlaThrGlyLysArgAlaAlaGluAspAspGlu | 450 |
| 451 | GATGACGATGTCGATACCAAGAAGCAGAAGACCGACGAGGATGACTAGAC<br>AspAspAspValAspThrLysLysGlnLysThrAspGluAspAspEnd | 500 |
| 501 | AGCAAAAAAGGAAAAGTTAAACTAAAAAAAAAAAAGGCCGCCGTGACCTAT | 550 |
| 551 | TCACCCTCCACTTCCCGTCTCAGAATCTAAACGTGGTCACCTTCGAGTAG | 600 |
| 601 | AGAGGCCCGCCCGCCCACCGTGGGCAGTGCCACCCGCAGATGACACGCGC | 650 |
| 651 | TCTCCACCACCCAACCCAAACCATGAGAATTTGCAACAGGGGAGGAAAAA | 700 |
| 701 | AGAACCAAAACTTCCAAGGCCCTGCTTTTTTTCTTAAAAGTACTTTAAAA | 750 |
| 751 | AGGAAATTTGTTTGTATTTTTTATTTACATTTTATATTTTTGTACATATT | 800 |
| 801 | GTTAGGGTCAGCCATTTTTAATGATCTCGGATGACCAAACCAGCCTTCGG | 850 |
| 851 | AGCGTTCTCTGTCCTACTTCTGACTTTACTTGTGGTGTGACCATGTTCAT | 900 |
| 901 | TATAATCTCAAAGGAGAAAAAAAACCTTGTAAAAAAAGCAAAAATGACAA | 950 |
| 951 | CAGAAAAACAATCTTATTCCGAGCATTCCAGTAACTTTTTTGTGTATGTA | 1000 |
| 1001 | CTTAGCTGTACTATAAGTAGTTGGTTTGTATGAGATGGTTAAAAAGGCCA | 1050 |
| 1051 | AAGATAAAAGGTTTCTTTTTTTTTCCTTTTTTGTCTATGAAGTTGCTGTT | 1100 |
| 1101 | TATTTTTTTTGGCCTGTTTGATGTATGTGTGAAACAATGTTGTCCAACAA | 1150 |
| 1151 | TAAACAGGAAT | 1161 |

III. Methods of Diagnosing, Prognosing or Monitoring the Course of Endometriosis

A. Introduction

Prothymosin expression is up-regulated in ectopic endometriotic tissue in endometriosis. This invention provides methods for diagnosing, prognosing or monitoring the course of endometriosis. Diagnostic methods involve detecting up-regulation of prothymosin by determining a test amount of a prothymosin gene product (e.g., mRNA, cDNA or polypeptide, including fragments thereof that may have resulted from degradation) in a biological sample from a patient or in the patient in situ, and comparing that amount with a normal amount or range for the prothymosin gene product. If the diagnostic amount is higher than the control amount, this is a positive sign in the diagnosis of endometriosis.

Methods of prognosing endometriosis also involve determining the amount of a prothymosin gene product in a biological sample from the patient. The method further involves comparing that amount to a prognostic amount. Various amounts of the gene product in a sample are consistent with certain prognoses for endometriosis. The detection of an amount of prothymosin mRNA or polypeptide at a particular prognostic level provides a prognosis for the subject.

Methods for monitoring the progress of endometriosis involve detecting the amount of a prothymosin gene product in the subject at a first and a second time, and comparing the amounts. A change in the amount indicates a change in the course of the disease, with a decreasing amount indicating remission of endometriosis and increase indicating progression of the endometriosis. Such assays are useful to evaluate the efficacy of a particular therapeutic intervention in patients being treated for endometriosis.

B. Sample Collection

A first step in a diagnostic or prognostic method is providing a biological sample to be tested. Increased expression of prothymosin in endometriosis can be detected in a variety of tissue and liquid biological samples. These include, for example, ectopic endometrial tissue and eutopic endometrial tissue (which express the gene product), peritoneal fluid (which can contain endometrial cells or their contents), vaginal secretions, urine or blood. Samples thus include cells (including whole cells, cell fractions, cell extracts), tissues, and tissue samples such as fme needle biopsy samples and body fluids. Biological samples may also include sections of tissues such as frozen sections taken for histological purposes.

A "biological sample" obtained from a patient can be referred to either as a "biological sample" or a "patient sample." It will be appreciated that analysis of a "patient sample" need not necessarily require removal of cells or tissue from the patient. For example, appropriately labeled prothymosin agents (e.g., antibodies or nucleic acids) can be administered into a patient and visualized (when bound to the target) using standard imaging technology (e.g., CAT, NMR, and the like.)

The sample may be pre-treated as necessary by dilution in an appropriate buffer solution or concentrated, if desired. Any of a number of standard aqueous buffer solutions, employing one of a variety of buffers, such as phosphate, Tris-buffer, or the like, at physiological pH can be used.

Assay formats using flow activated cell sorting ("FACS") or equivalent instruments or methods have advantages when measuring prothymosin gene products in a heterogeneous sample (such as a biopsy sample containing both normal and malignant cells).

C. Normal, Diagnostic, and Prognostic Values

In the assays of this invention, the prothymosin gene product is detected and optionally quantified to yield a "test amount." The test amount is then compared to a normal amount of prothymosin in the sample. An amount above a normal amount is a positive sign in a diagnosis of endometriosis. Particular methods of detection and quantitation are described below.

Normal or baseline levels or ranges of prothymosin expression can be determined for any particular sample type, patient or population. Generally, baseline (normal) levels of prothymosin protein or mRNA are determined by quantifying the amount of prothymosin protein and/or mRNA in a biological sample type from normal (healthy) subjects, e.g., a human subject. An amount of prothymosin gene product may be determined or expressed on a per sample volume basis, if the sample does not include cells. Preferably, it is determined or expressed on a per cell basis. To determine the cellularity of a sample, one can measure the level of a constitutively expressed gene product or other gene product expressed at known levels in cells of the type from which the sample was taken. Alternatively, normal values of prothymosin protein or prothymosin mRNA can be determined by quantifying the amount of prothymosin protein/RNA in cells or tissues known to be healthy, which are obtained from the same patient from whom diseased (or possibly diseased) cells are collected or from a healthy individual.

It will be appreciated that the assay methods do not necessarily require measurement of absolute values of prothymosin because relative values are sufficient for many applications of the methods of the present invention.

One of skill will appreciate that, in addition to the quantity or abundance of prothymosin gene products, variant or abnormal expression patterns or variant or abnormal expression products (e.g., mutated transcripts, truncated or nonsense polypeptides) may also be identified by comparison to normal expression levels and normal expression products.

D. Assays for Prothymosin Gene Products

The diagnostic and prognostic assays of this invention involve detecting and quantifying a prothymosin gene product from a patient sample. Prothymosin gene products include prothymosin mRNA or prothymosin protein. This section describes various methods of detecting and quantifying these products.

1. Polynucleotide Assays

In one embodiment, this invention provides for methods of detecting and/or quantifying expression of prothymosin mRNA or cDNA using amplification-based assays with or without signal amplification, hybridization based assays, and combination amplification-hybridization assays.

a. Preparation Of Polynucleotides

Polynucleotide assays are performed with a sample of nucleic acid isolated from the biological sample. The polynucleotide (e.g., genomic DNA, RNA or cDNA) may be isolated from the sample according to any of a number of methods well known to those of skill in the art. Methods for isolating nucleic acids are well known to those of skill in the art and are described, for example, Tijssen, P. ed. of Laboratory Techniques in Biochemistry and Molecular Biology: Hybridization With Nucleic Acid Probes, Part I. Theory and Nucleic Acid Preparation, Elsevier, N.Y. (1993) Chap. 3; Sambrook et al., Molecular Cloning, A laboratory Manual, 2nd edition, Cold Spring Harbor Laboratory, Cold Spring Harbor, N.Y. (1989) and Current Protocols in Molecular Biology, F. M. Ausubel et al., eds., (Current Protocols, a joint venture between Greene Publishing Associates, Inc. and John Wiley & Sons, Inc.).

In alternative embodiments, it is not necessary to isolate nucleic acids (e.g., total or polyA$_+$RNA) from the biological sample prior to carrying out amplification, hybridization or other assays. These embodiments have certain advantages when RNA is to be measured, because they reduce the possibility of loss of mRNA during isolation and handling. For example, many amplification techniques such as PCR and RT-PCR defmed above can be carried out using permeabilized cells (histological specimens and FACS analyses), whole lysed cells, or crude cell fractions such as certain cell extracts. Preferably, steps are taken to preserve the integrity of the target nucleic acid (e.g., mRNA) if necessary (e.g., addition of RNAase inhibitors). Amplification and hybridization assays can also be carried out in situ, for example, in thin tissue sections from a biopsy sample or from a cell monolayer (e.g., blood cells or dis-aggregated tissue culture cells). Amplification can also be carried out in an intact whole cell or fixed cells. For example, PCR, RT-PCR, or LCR amplification methods may be carrier out, as is well known in the art, in situ, e.g., using a polymerase or ligase, a primer or primer(s), and (deoxy)ribonucleoside triphosphates (if a polymerase is employed), and reverse transcriptase and primer (if RNA is to be transcribed and the cDNA is to be detected) on fixed, permeabilized, or microinjected cells to amplify target prothymosin RNA. This method is often useful when fluorescently-labeled dNTPs, primers, or other components are used in conjunction with microscopy, FACS analysis or the equivalent.

b. Amplification-based Assays

In one embodiment, the assays of the present invention are amplification-based assays for detection of a prothymosin gene product (e.g., mRNA or cDNA; hereinafter also referred to as "target"). In an amplification based assay, all or part of an polynucleotide target is amplified, and the amplification product is then detected directly or indirectly. This includes detecting the amplification product by hybridization with a probe, by detecting a product of the appropriate size on a gel or by mass spectrometry, for example, of by determining the sequence of at least a part of the amplification product. When there is no underlying gene product to act as a template, no amplification product is produced (e.g., of the expected size), or amplification is non-specific and typically there is no single amplification product. In contrast, when the underlying gene or gene product is present, the target sequence is amplified, providing an indication of the presence and/or quantity of the underlying gene or mRNA. Target amplification-based assays are well known to those of skill in the art.

Primers and probes for detecting prothymosin gene products may be designed and produced by those of skill by referring to the prothymosin sequence. Suitable primers and probes are sufficiently complementary to the prothymosin gene product to hybridize to the target nucleic acid. Primers are usually between about 10 and about 100 bases, typically between about 12 and about 50 bases, and may amplify all, or any portion, of the prothymosin gene product. Single oligomers (e.g., U.S. Pat. No. 5,545,522), nested sets of oligomers, or even a degenerate pool of oligomers may be employed for amplification. Two suitable primers for detecting prothymosin mRNA or cDNA sequences are: 5' primer: 5'—ctgacaatgaggtagacgaag—3' (SEQ ID NO:3); 3' primer: 5'—agtaaagtcagaagtaggac—3' (SEQ ID NO:4).

In one embodiment, a prothymosin gene product is amplified and detected using the polymerase chain reaction (including all variants, e.g., reverse-transcriptase-PCR; the Sunrise Amplification System (Oncor, Inc, Gaithersburg Md.); and numerous others known in the art). In one illustrative embodiment, PCR amplification is carried out in a 50 $\mu$l solution containing the nucleic acid sample (e.g., cDNA obtained through reverse transcription of mRNA), 100 $\mu$M in each dNTP (dATP, dCTP, dGTP and dTTP; Pharmacia LKB Biotechnology, N.J.), the mRNA-specific PCR primer(s), 1 unit/Taq polymerase (Perkin Elmer, Norwalk Conn.), 1×PCR buffer (50 mM KCI, 10 mM Tris, pH 8.3 at room temperature, 1.5 mM $MgCl_2$, 0.01 % gelatin) with the amplification run for about 30 cycles at 94° for 45 sec, 55° for 45 sec and 72° for 90 sec.

However, as will be appreciated, numerous variations may be made to optimize the PCR amplification for any particular reaction. Other suitable target amplification methods include the ligase chain reaction (LCR; e.g., Wu and Wallace, 1989, *Genomics* 4:560; Landegren et al., 1988, *Science*, 241: 1077, Barany, 1991, Proc. Natl. Acad. Sci. USA 88:189 and Barringer et al., 1990, *Gene*, 89: 117); strand displacement amplification (SDA; e.g., Walker et al., 1992, *Proc. Natl. Acad. Sci. U.S.A.* 89:392–396); transcription amplification (e.g., Kwoh et al., 1989, *Proc. Natil. Acad. Sci. USA*, 86: 1173); self-sustained sequence replication (3SR; e.g., Fahy et al., 1992, *PCR Methods Appl.* 1:25, Guatelli et al., 1990, *Proc. Nat'l. Acad. Sci. USA*, 87: 1874); the nucleic acid sequence based amplification (NASBA, Cangene, Mississauga, Ontario; e.g., Compton, 1991, *Nature* 350:91); the transcription-based amplification system (TAS); and the self-sustained sequence replication system (SSR).

One useful variant of PCR is PCR ELISA (e.g., Boehringer Mannheim Cat. No. 1 636 111) in which digoxigenin-dUTP is incorporated into the PCR product. The PCR reaction mixture is denatured and hybridized with a biotin-labeled oligonucleotide designed to anneal to an internal sequence of the PCR product. The hybridization products are immobilized on streptavidin coated plates and detected using anti-digoxigenin antibodies. Examples of techniques sufficient to direct persons of skill through in vitro amplification methods are found in PCR TECHNOLOGY: PRINCIPLES AND APPLICATIONS FOR DNA AMPLIFICATION, H. Erlich, Ed. Freeman Press, New York, N.Y. (1992); PCR PROTOCOLS: A GUIDE TO METHODS AND APPLICATIONS, eds. Innis, Gelfand, Snisky, and White, Academic Press, San Diego, Calif. (1990); Mattila et al., 1991, *Nucleic Acids Res.* 19: 4967; Eckert and Kunkel, (1991) PCR METHODS AND APPLICATIONS 1: 17; PCR, eds. McPherson, Quirkes, and Taylor, IRL Press, Oxford; U.S. Pat. Nos. 4,683,195, 4,683, 202, and 4,965,188; Barringer et al., 1990, *Gene*, 89:117; Lomell et al., 1989, *J. Clin. Chem.*, 35:1826.

Amplified products may be directly analyzed, e.g., by size as determined by gel electrophoresis; by hybridization to a target nucleic acid immobilized on a solid support such as a bead, membrane, slide, or chip; by sequencing; immunologically, e.g., by PCR-ELISA, by detection of a fluorescent, phosphorescent, or radioactive signal; or by any of a variety of other well-known means. For example, an illustrative example of a detection method uses PCR primers augmented with hairpin loops linked to fluorescein and a benzoic acid derivative that serves as a quencher, such that fluorescence is emitted only when the primers unfold to bind their targets and replication occurs.

In addition, methods are known to increase signal produced by amplification of the target sequence may be used. Methods for augmenting the ability to detect the amplified target include signal amplification system such as: branched DNA signal amplification (e.g., U.S. Pat. No. 5,124,246; Urdea, 1994, *Bio/Tech.* 12:926); tyramide signal amplification (TSA) system (DuPont); catalytic signal amplification (CSA; Dako); Q Beta Replicase systems (Tyagi et al., 1996, *Proc. Nat. Acad. Sci. USA*, 93: 5395 ); or the like.

One of skill in the art will appreciate that whatever amplification method is used, a variety of quantitative methods known in the art can be used if quantitation is desired. Detailed protocols for quantitative PCR may be found in PCR PROTOCOLS, A GUIDE TO METHODS AND APPLICATIONS, Innis et al., Academic Press, Inc. N.Y., (1990) and Ausubel et al., supra (Unit 15) and Diaco, R. (1995) Practical *Considerations for the Design of Quantitative PCR Assays*, in PCR STRATEGIES, pg. 84–108, Innis et al. eds, Academic Press, New York; and U.S. Patent No. 5,629,154.

c. Hybridization-based Assays

A variety of methods for specific DNA and RNA measurement using nucleic acid hybridization techniques are known to those of skill in the art (see Sambrook et al., supra). Hybridization based assays refer to assays in which a probe nucleic acid is hybridized to a target nucleic acid. Methods of selecting nucleic acid probe sequences for use in nucleic acid hybridization are discussed in Sambrook et al., supra and are based on the prothymosin gene sequence. In some formats, at least one of the target and probe is immobilized. The immobilized nucleic acid may be DNA, RNA, or another oligo- or poly-nucleotide, and may comprise natural or non-naturally occurring nucleotides, nucleotide analogs, or backbones. Such assays may be in any of several formats including: Southern, Northern, dot and slot blots, high-density polynucleotide or oligonucleotide arrays (e.g., GeneChips™ Affymetrix), dip sticks, pins, chips, or beads. All of these techniques are well known in the art and are the basis of many commercially available diagnostic kits. Hybridization techniques are generally described in Hames et al., ed., NUCLEIC ACID HYBRIDIZATION, A PRACTICAL APPROACH IRL Press, (1985); Gall and Pardue *Proc. Natl. Acad. Sci., U.S.A.*, 63: 378–383 (1969); and John et al., *Nature*, 223: 582–587 (1969).

One common format is direct hybridization, in which a target nucleic acid is hybridized to a labeled, complementary probe. Typically, labeled nucleic acids are used for hybridization, with the label providing the detectable signal. One method for evaluating the presence, absence, or quantity of prothymosin mRNA is carrying out a Northern transfer of RNA from a sample and hybridization of a labeled prothymosin-specific nucleic acid probe. Other common hybridization formats include sandwich assays and competition or displacement assays. Sandwich assays are commercially useful hybridization assays for detecting or isolating nucleic acid sequences. Such assays utilize a "capture" nucleic acid covalently immobilized to a solid support and a labeled "signal" nucleic acid in solution. The biological or clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The present invention also provides probe-based hybridization assays for prothymosin gene products employing arrays of immobilized oligonucleotide or polynucleotides to which a prothymosin nucleic acid can hybridize (i.e., to some, but usually not all or even most, of the immobilized oligo- or poly-nucleotides). High density oligonucleotide arrays or polynucleotide arrays provide a means for efficiently detecting the presence and characteristics (e.g., sequence) of a target nucleic acid (e.g., prothymosin gene, mRNA, or cDNA). Techniques are known for producing arrays containing thousands of oligonucleotides complementary to defmed sequences, at defmed locations on a surface using photolithographic techniques for synthesis in situ (see, e.g., U.S. Pat. Nos. 5,578,832; 5,556,752; and 5,510,270; Fodor et al., 1991, *Science* 251:767; Pease et al., 1994, *Proc. Natl. Acad. Sci. USA* 91:5022; and Lockhart et al., 1996, *Nature Biotech* 14:1675) or other methods for rapid synthesis and deposition of defmed oligonucleotides (Blanchard et al., 1996, *Biosensors & Bioelectronics* 11:687). When these methods are used, oligonucleotides (e.g., 20-mers) of known sequence are synthesized directly on a surface such as a derivatized glass slide. Usually, the array produced is redundant, having several oligonucleotide probes on the chip specific for the prothymosin polynucleotide to be detected.

An alternative means for detecting expression of a gene encoding a prothymosin protein is in situ hybridization. In situ hybridization assays are well known and are generally described in Angerer et al., METHODS ENZYMOL., 152: 649–660 (1987) and Ausubel et al., supra. In an in situ hybridization assay, cells or tissue specimens are fixed to a solid support, typically in a permeabilized state, typically on a glass slide. The cells are then contacted with a hybridization solution at a moderate temperature to permit annealing of labeled nucleic acid probes (e.g., $^{35}$S-labeled riboprobes, fluorescently labeled probes) completely or substantially complementary to prothymosin mRNA. Free probe is removed by washing and/or nuclease digestion, and bound probe is visualized directly on the slide by autoradiography or an appropriate imaging techniques, as is known in the art.

2. Prothymosin Polypeptide Assays a. Generally

The present invention provides methods and reagents for detecting and quantifying prothymosin polypeptides. These methods include analytical biochemical methods such as electrophoresis, mass spectroscopy, chromatographic methods and the like, or various immunological methods such as radioimmunoassay (RIA), enzyme-linked immunosorbent assays (ELISAs), immunofluorescent assays, western blotting, affinity capture mass spectrometry, biological activity and others described below and apparent to those of skill in the art upon review of this disclosure.

b. Immunoassays

The present invention also provides methods for detection of prothymosin polypeptides employing one or more anti-prothymosin antibody reagents (i.e., immunoassays). As used herein, an immunoassay is an assay that utilizes an antibody (as broadly defmed herein and specifically includes fragments, chimeras and other binding agents) that specifically binds a prothymosin polypeptide or epitope.

A number of well established immunological binding assay formats suitable for the practice of the invention are known (see, e.g., U.S. Pat. Nos. 4,366,241; 4,376,110; 4,517,288; and 4,837,168). See, e.g., METHODS IN CELL BIOLOGY VOLUME 37: ANTIBODIES IN CELL BIOLOGY, Asai, ed. Academic Press, Inc. New York (1993); BASIC AND CLINICAL IMMUNOLOGY 7th Edition, Stites & Terr, eds. (1991); Harlow and Lane, supra [e.g., Chapter 14], and Ausubel et al., supra, [e.g., Chapter 11]. Typically, immunological binding assays (or immunoassays) utilize a "capture agent" to specifically bind to and, often, immobilize the analyte to a solid phase. In one embodiment, the capture agent is a moiety that specifically binds to a prothymosin polypeptide or subsequence, such as an anti-prothymosin antibody.

Usually the prothymosin gene product being assayed is detected directly or indirectly using a detectable label. The particular label or detectable group used in the assay is usually not a critical aspect of the invention, so long as it does not significantly interfere with the specific binding of the antibody or antibodies used in the assay. The label may be covalently attached to the capture agent (e.g., an anti-prothymosin antibody), or may be attached to a third moiety, such as another antibody, that specifically binds to the prothymosin polypeptide.

The present invention provides methods and reagents for competitive and noncompetitive immunoassays for detecting prothymosin polypeptides. Noncompetitive immunoassays are assays in which the amount of captured analyte (in this case prothymosin) is directly measured. One such assay is a two-site, monoclonal-based immunoassay utilizing monoclonal antibodies reactive to two non-interfering epitopes on the prothymosin protein. See, e.g., Maddox et al., 1983, *J. Exp. Med.*, 158:1211 for background information. In one preferred "sandwich" assay, the capture agent (e.g., an anti-prothymosin antibody) is bound directly to a solid substrate where it is immobilized. These immobilized antibodies then capture any prothymosin protein present in the test sample. The prothymosin thus immobilized can then be labeled, i.e., by binding to a second anti-prothymosin antibody bearing a label. Alternatively, the second anti-prothymosin antibody may lack a label, but be bound by a labeled third antibody specific to antibodies of the species from which the second antibody is derived. The second antibody alternatively can be modified with a detectable moiety, such as biotin, to which a third labeled molecule can specifically bind, such as enzyme-labeled streptavidin.

In competitive assays, the amount of prothymosin protein present in the sample is measured indirectly by measuring the amount of an added (exogenous) prothymosin displaced (or competed away) from a capture agent (e.g., anti-prothymosin antibody) by the prothymosin protein present in the sample.

A hapten inhibition assay is another example of a competitive assay. In this assay prothymosin protein is immobilized on a solid substrate. A known amount of anti-prothymosin antibody is added to the sample, and the sample is then contacted with the immobilized prothymosin protein. In this case, the amount of anti-prothymosin antibody bound to the immobilized prothymosin protein is inversely proportional to the amount of prothymosin protein present in the sample. The amount of immobilized antibody may be detected by detecting either the immobilized fraction of antibody or the fraction of the antibody that remains in solution. In this aspect, detection may be direct, where the antibody is labeled, or indirect where the label is bound to a molecule that specifically binds to the antibody as described above.

c. Other Antibody-based Assay Formats

The invention also provides reagents and methods for detecting and quantifying the presence of prothymosin polypeptide in the sample by using an immunoblot (Western blot) format. Another immunoassay is the so-called "lateral flow chromatography." In a non-competitive version of lateral flow chromatography, a sample moves across a substrate by, e.g., capillary action, and encounters a mobile labeled antibody that binds the analyte forming a conjugate. The conjugate then moves across the substrate and encounters an immobilized second antibody that binds the analyte. Thus, immobilized analyte is detected by detecting the labeled antibody. In a competitive version of lateral flow chromatography a labeled version of the analyte moves across the carrier and competes with unlabeled analyte for binding with the immobilized antibody. The greater the amount of the analyte in the sample, the less the binding by labeled analyte and, therefore, the weaker the signal. See, e.g., May et al., U.S. Pat. No. 5,622,871 and Rosenstein, U.S. Pat. No. 5,591,645.

d. Solid Phases: Substrates, Solid Supports, Membranes, Filters

As noted supra, depending upon the assay, various components, including the antigen, target antibody, or anti-prothymosin antibody, may be bound to a solid surface or support (i.e., a substrate, membrane, or filter paper). Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

e. Mass Spectrometry

The mass of a molecule frequently can be used as an identifier of the molecule. Therefore, methods of mass spectrometry can be used to identify a protein analyte. Mass spectrometers can measure mass by determining the time required for an ionized analyte to travel down a flight tube and to be detected by an ion detector.

One method of mass spectrometry for proteins is matrix-assisted laser desorption/ionization mass spectrometry ("MALDI"). In MALDI the analyte is mixed with an energy absorbing matrix material that absorbs energy of the wavelength of a laser and placed on the surface of a probe. Upon striking the matrix with the laser, the analyte is desorbed from the probe surface, ionized, and detected by the ion detector. See, for example, Hillenkamp et al., U.S. Pat.No. 5,118,937.

Other methods of mass spectrometry for proteins are described in Hutchens and Yip, U.S. Pat. No. 5,719,060. In one such method referred to as Surfaces Enhanced for Affinity Capture ("SEAC") a solid phase affinity reagent that binds the analyte specifically or non-specifically, such as an antibody or a metal ion, is used to separate the analyte from other materials in a sample. Then the captured analyte is desorbed from the solid phase by, e.g., laser energy, ionized, and detected by the detector.

3. Assay Combinations

The diagnostic and prognostic assays described herein can be carried out in various combinations and can also be carried out in conjunction with other diagnostic or prognostic tests. For example, when the present methods are used to diagnose endometriosis, the presence of a prothymosin gene product can be used to determine the stage of the disease. Tests that may provide additional information include microscopic analysis of biopsy samples, detection of antigens (e.g., cell-surface markers) associated with endometriosis (e.g., using histocytochemistry, FACS, or the like).

E. In Vivo Diagnosis and Treatment

In another method of the invention, endometriosis can be diagnosed in vivo. The methods involve detecting binding between a prothymosin gene product and compound that specifically binds the product. The compound also includes a detectable label. In general, any conventional method for visualizing diagnostic imaging can be used. In one method, detection is performed by laparoscopy. The compound is introduced into the subject at the site of a suspected lesion and binding is detected using the laparoscope. Alternatively, the binding can be detected by, for example, magnetic resonance imaging (MRI) or electron spin resonance (ESR). Usually gamma-emitting and positron-emitting radioisotopes are used for camera imaging and paramagnetic isotopes are used for magnetic resonance imaging. Any amount of binding above background is a positive sign of endometriosis. Persons of skill in the art recognize that not every positive sign results in a definitive diagnosis of a disease.

Endometriotic lesions can be removed surgically. However, lesions may be tiny, and difficult to identify by eye. This invention takes advantage of prothymosin as marker for endometriosis by providing a method to identify and remove endometriotic lesions. The method involves identifying endometriotic lesions in situ using a labeled probe directed to a prothymosin gene product and removing them surgically.

In the practice of this method, a probe is provided. The probe binds to a prothymosin gene product and is labeled with a detectable marker that can be detected in a surgical procedure. The probe preferably is directed to prothymosin polypeptide, but can be directed to prothymosin mRNA. In particular, the probe can be an antibody that specifically binds prothymosin. A preferred label that can be detected during surgery is a radioactive label. Such labels can be identified with the use of, e.g., a Geiger counter.

Surgery can proceed as follows. The labeled probe is introduced into the peritoneum of the patient for a time sufficient for the label to bind to endometriotic lesions. Unbound labeled probe is washed out. Then, endometriotic lesions are identified using a suitable detector. For example, in laparoscopic surgery, a Geiger counter may be introduced through the incision. Radioactive ("hot") spots indicate bound labeled and, therefore, an endometriotic lesion. These lesions are then removed from the patient.

F. Kits

The present invention also provides kits useful for the screening, monitoring, diagnosis and prognosis of patients with endometriosis. The kits include one or more reagents for detecting a prothymosin gene product (mRNA, cDNA or protein) or for quantifying expression of prothymosin. They further include instructions for using the amount of prothymosin gene product detected for diagnosing, prognosing or monitoring the course of endometriosis.

Reagents for detecting a prothymosin gene product include any reagents described herein. Reagents for detecting polynucleotides include, for example, polynucleotide probes and primers that specifically bind to the prothymosin gene, RNA, cDNA, or portions thereof. Reagents for detecting prothymosin polypeptides include, for example, affinity agents, antibodies and protein ligands.

Other materials in the can include reagents for carrying out the assays. These materials include, for example, reverse transcriptases, DNA polymerases, ligases), buffers, reagents (labels, dNTPs), etc. Polynucleotide or protein probes can be conjugated to another moiety such as a label and/or it can be immobilized on a solid phase. Kits may also contain a second antibody for detection of prothymosin polypeptide/antibody complexes or for detection of hybridized nucleic acid probes, as well as one or more prothymosin peptides or proteins for use as control or other reagents.

Examples of such formats include those that detect a signal by histology (e.g., immunohistochemistry with signal-enhancing or target-enhancing amplification steps) or fluorescence-activated cell analysis or cell sorting (FACS). These formats are particularly advantageous when dealing with a highly heterogeneous cell population (e.g., containing multiple cells types in which only one or a few types have elevated prothymosin levels, or a population of similar cells expressing prothymosin at different levels).

IV. Screening for Compounds that Inhibit Prothymosin Expression in Endometrial Cells Compounds that inhibit expression of a prothymosin gene product in endometrial cells are useful in the treatment of endometriosis. This invention provides methods of screening compounds for their ability to inhibit such expression. The methods involve contacting an endometrial cell that expresses a prothymosin gene product with the compound, and determining whether the compound modulates expression of the gene product.

A. Tissue Sample

In a preferred embodiment the tissue is human endometrial tissue that is cultured in an immunodeficient mouse. The compound is administered to the mouse. Then, the tissue is examined to determine expression of the prothymosin gene product. The mouse model is described in more detail in Example I. Alternatively, the compound can be screened in vitro using tissue from endometriotic lesions.

B. Test Agents

A test agent that is to be screened for its ability to modulate prothymosin expression is administered to the test animal or to the cultured cells in vitro. The choice of the agent to be tested is left to the discretion of the practitioner. However, because of their variety and ease of administration as pharmaceuticals, small molecules are preferred as test agents.

1. Chemistry

The agent to be tested can be selected from a number of sources. For example, combinatorial libraries of molecules are available for screening. Using such libraries, thousands of molecules can be screened for regulatory activity. In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) Nature Biotechnology, 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

2. Route of Administration

When the tissue is cultured as an endometrial xenograft, the agent can be administered by any route that gives it access to the tissue. In one embodiment, the agent is delivered to the peritoneal cavity where the xenograft has been implanted. However, the agent can be delivered by any potential route if the agent becomes a drug for use in ultimate treatment of endometriosis. The agent can be administered in the form of a pharmaceutical composition. This includes, for example, aqueous solutions for enteral, parenteral or transmucosal administration, e.g., for intravenous administration, as tonics and administration to mucous or other membranes as, for example, nose or eye drops; solid and other non-aqueous compositions for enteral or transdermal delivery, e.g., as pills, tablets, powders or capsules; transdermal or transmucosal delivery systems for topical administration, and aerosols or mists for delivery by inhalation. One advantage of delivery by a mode that is easy to administer, e.g., enteral or by intravenous or intramuscular injection is that such modes mimic possible modes of delivery should the agent be formulated as a pharmaceutical.

C. Detecting Expression of Prothymosin

After sufficient time has elapsed, the culture cells or explant tissue is tested to detect the presence and/or amount of expression of a prothymosin gene product. Usually, this time will be between about 6 minutes and about 10 days. When the tissue is being cultured in an immunodeficient mouse, the xenograft preferably is removed from the animal and analyzed in vitro. Detecting the prothymosin gene product can be accomplished by any method described known in the art or described herein.

D. Determining Whether The Agent Modulates Prothymosin Expression

The amount of prothymosin expression test and control tissue is determined. These amounts are recorded and subject to statistical analysis to determine whether any difference is statistically significant. A statistically significant difference ($p<0.05$) indicates that the agent modulates the expression of prothymosin in endometrial tissue. Thus, one can determine whether the agent reduces, increases or has no effect on the amount of prothymosin expression in an tissue. Agents identified to inhibit prothymosin expression are candidates as drugs for the prophylactic and therapeutic treatment of endometriosis.

Agents can be subject to further analysis by, for example, studying their effect under more discriminating conditions, or by altering the agent to create a "second generation" agent for testing. Agents also can be tested in combination with other agents. The effect of the agent on other aspects of animal physiology also can be tested.

V. Inhibitory Polynucleotides

A. General

Inhibitory polynucleotides directed against prothymosin gene or mRNA are useful in treating endometriosis. Inhibitory polynucleotides can inhibit prothymosin activity in a number of ways. According to one mechanism, the polynucleotide prevents transcription of the prothymosin gene (for instance, by triple helix formation). In another mechanism, the polynucleotide destabilizes the prothymosin and reduces its half-life. The polynucleotides can be directed to the coding region or adjacent non-coding regions, such as 5' up-stream region that contains expression control sequences.

An inhibitory polynucleotide is a polynucleotide that is capable of hybridizing under stringent conditions with a target polynucleotide and that interferes with the transcription, processing, translation or other activity the target polynucleotide. Inhibitory polynucleotides generally are single-stranded and have a sequence of at least 7, 8, 9, 10, or 11 nucleotides capable of specifically hybridizing to the target sequence. RNA sequences generally require a sequence of at least 10 nucleotides for specific hybridization. Inhibitory polynucleotides include, without limitation, antisense molecules, ribozymes, sense molecules and triplex-forming molecules.

While not wishing to be limited by theory, it is believed that inhibitory polynucleotides inhibit the function of a target, in part, by binding to the appropriate target sequence. An inhibitory polynucleotide can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote inhibitory mechanisms of the cells, such as promoting RNA degradation via RNase action. The inhibitory polynucleotide can bind to the major groove of the duplex DNA to form a triple helical or "triplex" structure. Methods of inhibition using inhibitory polynucleotides therefore encompass a number of different approaches to altering expression of specific genes that operate by different mechanisms. These different types of inhibitory polynucleotide technology are described in C. Helene and J. Toulme, (1990) *Biochim. Biophys. Acta*., 1049:99–125.

The literature also provides examples of antisense polynucleotide inhibition of the function of ribonucleoproteins. Hence, for ribonucleoprotein complexes that contain a functional RNA (e.g., snRNP complexes involved in RNA splicing), it has been shown that antisense polynucleotides can inhibit in vitro activity (e.g., splicing).

Antisense polynucleotides can be DNA or RNA. They can be chemically modified so as to improve stability in the body. Properties of the polynucleotide can be engineered to impart stability (e.g., nuclease resistance), tighter binding or the desired $T_m$. For example, the polynucleotide can include modified nucleotide analogs, such as those already described. The polynucleotide can comprise mixtures of naturally occurring nucleotides and nucleotide analogues. Other techniques for rendering polynucleotides nuclease-resistant include those described in International patent publication No. 94/12633.

The general approach to constructing various polynucleotides useful in inhibitory polynucleotide therapy has been reviewed by A. R. Vander Krol et al. (1988), *Biolechniques* 6:958–976, and by C. A. Stein et al., (1988) *Cancer Res.* (1988) 48:2659–2668. See also *Oligodeoxynucleotides: Antisense Inhibitors of Gene Expression*, Cohen, J. S., editor, MacMillan Press, London, pages 79–196 (1989), and Antisense RNA and DNA, (1988), D. A. Melton, Ed., Cold Spring Harbor Laboratory, Cold Spring Harbor, N.Y.

In certain embodiments inhibitory polynucleotides comprise a derivatized substituent which is substantially non-interfering with respect to hybridization of the inhibitory polynucleotide to the target polynucleotide. Typically such inhibitory polynucleotides are derivatized, and additional chemical substituents are attached, either during or after polynucleotide synthesis, respectively, and are thus localized to a complementary sequence in the target polynucleotide where they produce an alteration or chemical modification to a local DNA sequence and/or to a protein component.

Preferred attached chemical substituents include: europium (III) texaphyrin, cross-linking agents, psoralen, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are particularly preferred chemical substituents where local cleavage of a polynucleotide sequence is desired (Hertzberg et al. (1982) *J. Am. Chem. Soc.* 104:313; Hertzberg and Dervan (1984) *Biochemistry* 23:3934; Taylor et al. (1984) *Tetrahedron* 40:457; P. B. Dervan (1986) *Science* 232:464).

Preferred attachment chemistries include: direct linkage, e.g., via an appended reactive arnino group (Corey and Schultz (1988) *Science* 238:1401) and other direct linkage chemistries, although streptavidin/biotin and digoxigenin/anti-digoxigenin antibody linkage methods may also be used. Methods for linking chemical substituents are provided in U.S. Pat. Nos. 5,135,720, 5,093,245, and 5,055,556. Other linkage chemistries may be used at the discretion of the practitioner.

B. Antisense

This invention provides antisense polynucleotides capable of specifically hybridizing to a target sequence of prothymosin, e.g., prothymosin. Antisense polynucleotides are useful in vitro or in vivo to inhibit the activity of prothymosin.

The antisense polynucleotides of this invention comprise an antisense sequence of at least 7 nucleotides that specifically hybridize to a sequence from prothymosin and, more particularly, mammalian prothymosin and human prothymosin. In one aspect of the invention, the RNA sequence to which the antisense sequence specifically hybridizes to a coding or non-coding region of the prothymosin gene or mRNA.

The antisense sequence can be between about 10 and about 50 nucleotides or between about 15 and about 35 nucleotides. In one embodiment, the sequence of the polypeptide contains within it the antisense sequence. In this case, the antisense sequence is contained within a polynucleotide of longer sequence. In another embodiment, the sequence of the polypeptide consists essentially of, or is, the antisense sequence. Thus, for example, the antisense polynucleotide can be a polynucleotide of less than about 50 nucleotides in a sequence that specifically hybridizes to the target sequence.

Generally, to assure specific hybridization, the antisense sequence is substantially complementary to the target sequence in prothymosin. In certain embodiments, the antisense sequence is exactly complementary to the target sequence. The antisense polynucleotides may include nucleotide substitutions, additions, deletions, or transpositions, so long as specific binding to the relevant target sequence corresponding to prothymosin or its gene is retained as a functional property of the polynucleotide.

The antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothioate, etc.), among others. Antisense polynucleotides of the invention are polynucleotides of at least 7 nucleotides and can be between about 10 and 50 nucleotides or between about 15 and 30 nucleotides. In other embodiments, antisense polynucleotides are polynucleotides of less than about 100 nucleotides or less than about 200 nucleotides.

Accordingly, a sequence of the antisense polynucleotide can specifically hybridize to all or part of the prothymosin sequence, such as antisense polynucleotides to the human prothymosin gene or its transcribed RNA, including truncated forms which may be associated with prothymosin ribonucleoprotein.

For general methods relating to antisense polynucleotides, see *Antisense RNA and DNA*, (1988), D. A. Melton, Ed., Cold Spring Harbor Laboratory, Cold Spring Harbor, N.Y.). For a review of antisense therapy, see, e.g., Uhlnann et al., *Chem. Reviews*, 90:543–584 (1990).

The formation of a double-stranded polynucleotide resulting from hybridization of an antisense DNA molecule to prothymosin renders prothymosin susceptible to RNase H cleavage. Accordingly, antisense polynucleotides directed against prothymosin are particularly effective for inhibiting prothymosin activity in cells or samples containing RNase H.

C. Ribozymes

Cleavage of prothymosin can be induced by the use of ribozymes or catalytic RNA. In this approach, the ribozyme would contain either naturally occurring RNA (ribozymes) or synthetic nucleic acids with catalytic activity. Bratty et al., (1992) *Biochim. Biophys. Acta.*, 1216:345–59 (1993) and Denhardt, (1992) *Ann. N.Y. Acad. Sci.*, 660:70–76 describe methods for making ribozymes.

Unlike the antisense and other polynucleotides described above, which bind to an RNA, a DNA, or a prothymosin protein component, a ribozyme not only binds but also specifically cleaves and thereby potentially inactivates a target RNA. Such a ribozyme can comprise 5'- and 3'-terminal sequences complementary to the prothymosin RNA.

Depending on the site of cleavage, a ribozyme can render the prothymosin enzyme inactive. Upon review of the RNA sequence of the human prothymosin those in the art will note that several useful ribozyme target sites are present and susceptible to cleavage by, for example, a hammerhead motif ribozyme. Optimum target sites for ribozyme-mediated inhibition of prothymosin activity can be determined as described by Sullivan et al., PCT patent publication No. 94/02595 and Draper et al., PCT patent publication No. 93/23569. As described by Hu et al., PCT patent publication No. 94/03596, antisense and ribozyme functions can be combined in a single polynucleotide.

Such engineered ribozymes can be expressed in cells or can be transferred by a variety of means (e.g., liposomes, immunoliposomes, biolistics, direct uptake into cells, etc.). Other forms of ribozymes (group I intron ribozymes (Cech (1995) *Biotechnology* 13; 323); hammerhead ribozymes (Edgington (1992) *Biotechnology* 10: 256) can be engineered on the basis of the disclosed prothymosin sequence information to catalyze cleavage of prothymosin.

D. Other Inhibitory Polynucleotides

In addition to the antisense and ribozyme inhibitory polynucleotides, one can construct polynucleotides that will bind to duplex nucleic acid either in the folded. RNA or in the gene for the RNA, forming a triple helix-containing or triplex nucleic acid to inhibit prothymosin activity. Such polynucleotides of the invention are constructed using the base-pairing rules of triple helix formation and the nucleotide sequence of target gene. (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci.* (U.S.A.) 83: 9591.) Such polynucleotides can block prothymosin activity in a number of ways, including by preventing transcription of the prothymosin gene. Typically, and depending on mode of action, the triplex-forming polynucleotides of the invention comprise a sequence large enough to form a stable triple helix but small enough, depending on the mode of delivery, to administer in vivo.

E. Methods of Making Inhibitory Polynucleotides

Inhibitory polynucleotides can be made chemically or recombinantly.

1. Chemical synthesis

Small inhibitory polynucleotides for direct delivery can be made by chemical synthesis. Chemically synthesized polynucleotides can be DNA or RNA, or can include nucleotide analogs or backbones that are not limited to phosphodiester linkages.

2. Recombinant production

For delivery into cells or for gene therapy methods, recombinant production of inhibitory polynucleotides through the use of expression vectors is particularly useful. Accordingly, this invention also provides expression vectors, e.g., recombinant nucleic acid molecules comprising expression control sequences operatively linked to the nucleotide sequence encoding the inhibitory polynucleotide. Expression vectors can be adapted for function in prokaryotes or eukaryotes (e.g., bacterial, mammalian, yeast, Aspergillus, and insect cells) by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989), *Current Protocols in Molecular Biology*, F. M. Ausubel et al., eds., (Current Protocols, a joint venture between Greene Publishing Associates, Inc. and John Wiley & Sons, Inc.) and Berger and Kimmel, *Methods in Enzymology, Volume* 152, *Guide to Molecular Cloning Techniques* (1987), Academic Press, Inc., San Diego, Calif. Useful promoters for such purposes include a metallothionein promoter, a constitutive adenovirus major late promoter, a dexamethasone-inducible MMTV promoter, a SV40 promoter, a MRP polII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes. Recombinant DNA expression plasmids can also be used to prepare the polynucleotides of the invention for delivery by means other than by gene therapy, although it may be more economical to make short oligonucleotides by in vitro chemical synthesis.

Methods of transfecting genes into mammalian cells and obtaining their expression for in vitro use or for gene therapy, are well known to the art. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990). Cells can be transfected with plasmid vectors, for example, by electroporation. Cells can be transfected by polynucleotides by calcium phosphate precipitation DNA liposome complexes, by particle-mediated gene transfer (biolistics) or with liposomes.

Expression vectors useful in this invention depend on their intended use. Such expression vectors must, of course, contain expression and replication signals compatible with the host cell. Expression vectors useful for expressing the inhibitory polynucleotide of this invention include viral vectors such as retroviruses, adenoviruses and adeno-associated viruses, plasmid vectors, cosmids, liposomes and the like. Viral and plasmid vectors are preferred for transfecting mammalian cells. The expression vector pcDNA1 (Invitrogen, San Diego, Calif.), in which the expression control sequence comprises the CMV promoter, provides good rates of transection and expression. Adeno-associated viral vectors are useful in the gene therapy methods of this invention.

F. In Cells

Inhibitory polynucleotides against prothymosin are useful for inhibiting prothymosin activity in both cultured cells and in cells in vivo. The inhibition of prothymosin activity in cells in vivo is useful in prophylactic and therapeutic methods of treating endometriosis.

This invention contemplates a variety of means for delivering an inhibitory polynucleotide to a subject including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory nucleic acid.

One can provide a cell with an inhibitory polynucleotide by contacting the cell with a soluble inhibitory nucleic acid, for example, in the culture medium in vitro or in the circulatory system, interstitial fluid or tissue mass in vivo. Soluble inhibitory nucleic acids present in the external milieu have been shown to gain access to the cytoplasm. Methods useful for delivery of polynucleotides for therapeutic purposes are described in Inouye et al., U.S. Pat. No. 5,272,065.

VI. Methods of Inhibiting Prothymosin Expression

This invention provides methods of inhibiting prothymosin activity in endometrial cells either in vitro, ex vivo or in vivo. The methods involve contacting the cells with an agent that inhibits prothymosin expression. The agent can be any compound or composition that inhibits prothymosin expression, including inhibitory polynucleotide, small molecules and prothymosin ligands, such as an antibody that specifically binds prothymosin, thereby inhibiting its activity. Inhibiting prothymosin in endometrial cells in vitro is useful in inhibiting cell proliferation. Inhibiting prothymosin in vivo is useful as a therapy against endometriosis.

VII. Prophylactic and Therapeutic Methods

This invention provides methods of inhibiting prothymosin expression for treating endometriosis. The methods involve administering to the subject an agent (e.g., a compound) that inhibits expression of prothymosin in an amount effective to inhibit prothymosin activity (a "pharmacologically effective amount"). Cells that express prothymosin activity and that can be targets of prothymosin inhibition therapy include eutopic and ectopic endometrial cells. Such agents include small molecules, inhibitory polynucleotides, or antibodies or other ligands than bind prothymosin polypeptides.

A. Administration

Inhibitory compounds can be delivered conveniently in the form of a pharmaceutical composition comprising a pharmaceutically acceptable carrier and a pharmacologically effective amount of the agent. The pharmaceutical composition can be administered by any means known in the art for delivery of such molecules. However, systemic administration by injection is preferred. Because endometriotic lesions occur in the peritoneum, most preferably, this is intraperitoneal administration. However, other systemic routes of administration include intramuscular, intravenous, and subcutaneous injection. The pharmaceutical compositions can be administered in a variety of unit dosage forms depending upon the method of administration. For example, unit dosage forms for parenteral administration include unit doses of injectable solutions.

The form, amounts and timing of administration generally are a matter for determination by the practitioner. In one embodiment, the pharmaceutical composition is delivered as a unit dosage form. In the case of polynucleotides or vectors used in gene therapy, doses can be escalated until an optimal dose is determined. Dosages of about of to 1013 particles of viral vector per ml of carrier are effective. Systemic administration can be from about 0.1 mg/kg to about 2.0 mg/kg per day. However, when delivered directly to the site (e.g., peritoneum) the amount can be less. The volume administered can be selected by the practitioner. According to one embodiment of this invention, approximately $10^{10}$ vectors suspended in about 1 ml of sterile PBS constitute a therapeutically effective amount.

The attending physician can determine the amount of the polynucleotide to deliver. Low doses are initially administered to observe patient response.

EXAMPLES

The following examples are offered by way of illustration, not by way of limitation.

I. The Endometriosis Mouse Model

The endornetriosis mouse model is prepared or generated by a method which comprises: a) eliminating endogenous progesterone from a severely compromised immune deficient (SCID) female mouse; b) adding a micronized exogenous estrogen source to a xenograft of human normal endometrial tissue; c) implanting the xenograft into the intraperitoneal cavity of the mouse; d) adding an exogenous estrogen source to the mouse before and after implantation of the xenograft; and e) allowing the xenograft to grow and mimic the progression of human endometriosis tissue. The length of time for progression is typically 3 to 7 weeks, preferably about 5 weeks.

Usually the endogenous progesterone is eliminated from the SCID mouse by a bilateral oophorectomy or by administration of an anti-progesterone agent. The mouse selected for the model is a female mouse in which her immune system is severely compromised, so that the implanted xenograft will be accepted, grow and develop.

In preparing the xenograft, a section of human normal endometrial tissue is identified, isolated from its human donor, and fragmented, and then an exogenous source of estrogen is added. Typically, this estrogen is micronized and is in water-soluble form prior to its administration or addition to the xenograft.

The prepared xenograft is implanted or transplanted into the intraperitoneal cavity of the mouse and exogenous estrogen is administered to the mouse both before and after implantation. The xenograft then grows and develops in the mouse, mimicking the progression of human endometriosis. Approximately from about 0.05 to about 1.5 cubic centimeters (cc) of the solid tissue is isolated with the xenograft optionally suspended in a physiologically-compatible solution or nutrient medium and the suspension injected into each mouse at an amount from about 0.4 cc to about 0.6, cc so that the mouse receives about 0.2 cc of material. Also, an antibiotic can be administered to the mouse in conjunction with the xenograft implantation.

The source of the xenograft tissue is from a human female; usually the result of a hysterectomy or an endometrial biopsy. Preferably, the xenograft is obtained from a pre-menopausal female not previously treated with gonadotropin-releasing hormone (GnRH) agonists.

Various sources of exogenous estrogen can be used, such as beta-estradiol-17-cypionate, poly-estradiol phosphate, beta-estradiol benzoate, and the like, and is administered to the xenograft and the mouse in different dosages and methods. The estrogen is added to the xenograft in a water-soluble or micronized form to reach a concentration from about 50 to about 500 nanomolars (nM); whereas the mouse receives from about 60 micrograms (μg) per kilogram (kg) per week to about 120 ug per kg per week of exogenous estrogen. The estrogen is administered intramuscularly or subcutaneously to the mouse starting at least one day prior to the implantation of the xenograft and continuing once a week after implantation.

The xenograft tissue was removed from the mice and mRNA was isolated. Subtractive hybridization was performed using cDNA from normal human endometrial tissue and from normal mouse tissue as a driver, and using the explant cDNA as a tester. An endometrial carcinoma cell line cDNA library was screened with the subtractive probe. One of the clones that hybridized to the probe was isolated and identified as encoding prothymosin.

II. Evidence That Prothymosin in Up-Regulated in Human Tissue Cultivated in Mice We discovered that prothymosin is up-regulated in human endometrial tissue cultivated in an immunodeficient mouse. After cultivation, cDNA from the tissue was used as a Tester and subtracted with cDNA from normal human endometrial tissue and cDNA from normal mouse tissue as a Driver. The subtracted library was used to probe an endometrial carcinoma cDNA library. One clone to which the probe hybridized was isolated. Upon analysis, the clone proved to encode prothymosin.

Suppression subtractive hybridization (SSH) was used to identify endometriosis-specific sequences by using material obtained from the endometriosis mouse model. The SSH method had to be slightly modified such that normal mouse RNA was mixed with the normal endometrial RNA, to allow for the complete subtraction of normal human endometrium and normal mouse sequences from the endometrial explants. The SSH PCR based cDNA subtraction protocol was performed using the Clontech PCR-Select kit (Palo Alto, Calif.) and included using material from explant (Tester), normal endometrium (Driver) and normal mouse (Driver) tissue. Briefly, approximately 500 ng of poly A selected mRNA from each tissue was used as template for cDNA synthesis with 10 μmol of the kit supplied cDNA synthesis primer and MMLV reverse transcriptase. Following a 1.5 hr incubation at 42° C., the cDNA was incubated with DNA polymerase for 30 min at 16° C. to generate the second cDNA strand. The double stranded DNA was phenol/chloroform extracted and precipitated with ethanol, followed by one wash with 80% ethanol and re-suspension into 9 μl of water. The 9 μl of cDNA was subjected to a 1.5 hr digestion with Rsa at 37° C., followed by phenol/chloroform extraction and precipitation with ethanol as described above. The Driver cDNA from normal endometrium and normal mouse tissue was complete after the precipitation step.

For the Tester cDNA, adapter linkers were ligated onto the ends of the Rsa digested cDNA by mixing a 2 μl portion of the digested cDNA with 10 μmole of either adapter 1 or adapter 2 and incubating in the presence of ligase for 16 hrs at 14° C., which completed the generation of the Tester cDNA populations (TS1 and TS2). Each Tester cDNA population was hybridized separately with the mixed Driver cDNA (at a ratio of 1:1, mouse Driver: normal Driver). Following an 8 hour incubation at 68° C., the two separate cDNA Tester (TS1 or TS2)—Driver mixtures were mixed together and hybridized at 68° C. for an additional 16 hrs. The hybridization mixture was used as template for PCR amplification using primers that mapped to adapter 1 and adapter 2 using standard conditions. The PCR amplicon was used as a template for the production of a random-prime radiolabeled probe that was used to screen an RL95-2 (endometrial carcinoma cell line) cDNA library.

The RL95-2 (endometrial carcinoma cell line) Lambda-Zap cDNA library was screened using standard protocols suggested by the manufacturer (Stratagene, La Jolla, Calif.). Briefly, approximately $10^6$ infectious phage particles were incubated with XL-1 blue host cells and plated at density of 50,000 phage per 150 mm dish using standard protocols (Stratagene). The phage particles were transferred to a nylon membrane, blocked in hybridization solution and incubated with radiolabeled subtracted probe. Following several washing steps, the membranes were exposed to X-ray film and the positive plaques were identified, cored and plated. One such clone was named "Repro-EN-203." To insure that the selected phage plaque represented a single clone the screening process was repeated three times as described above. Plasmid containing the cDNA insert was excised from the phage clone using the manufacturer's protocols (Stratagene). The size of the cloned insert was determined by releasing the cDNA fragment from the rescued pBluescript Repro-EN-203 plasmid with the restriction enzymes EcoRI and XhoI. The released insert was size fractionated by agarose-gel electrophoresis and the apparent length of the insert was determined by comparing its migration position with a DNA standard (1 kb ladder; Gibco BRL). The insert migrated at approximately 1.2 Kb. The nucleotide sequence of the cloned insert was determined by using a modified protocol of the dideoxy chain termination method of Sanger et al. and USB Sequenase 2.0 (Barker, D. F. (1993) Biotechniques). The amino acid sequence was predicted using the Bionet Intelligenetics suite (Oxford Molecular Group).

III. A Protocol for Detecting Prothymosin mRNA in a Sample Using RT-PCR

In one aspect, this invention provides a method for diagnosing endometriosis that involves detecting prothymosin mRNA in a patient sample. Presented here is a protocol for performing RT-PCT to detect prothymosin mRNA.

A. Materials Provided

Primers for prothymosin:

5' primer: 5'—ctgacaatgaggtagacgaag—3' (SEQ ID NO:3).

3' primer: 5'—agtaaagtcagaagtaggac—3' (SEQ ID NO:4)

cDNA synthesis kit components including RT enzyme

PCR kit components including polymerase cDNA control material

B. Protocols 1. cDNA Synthesis (RT)

To a microfuge tube add the following materials and amounts:

| Component | Volume per reaction |
|---|---|
| sample RNA (see note) | 2 μL |
| RT primer (50 ng/μL) | 2 μL |
| RNase free water | 8 μL |
| total volume | 12 μL |

Note: This assumes a concentration of 1 μg/μL. If the concentration is different, adjust the amount of RNA and water added accordingly.

Incubate at 70° C. in a water bath for 10 minutes and snap cool on ice for at least 1 minute.

Prepare a master mix with the following materials and amounts in the order indicated. Prepare enough of the mix for one extra reaction.

| Component | Volume per reaction |
|---|---|
| 10 × PCR Buffer | 2 μL |
| 25 mM $MgCl_2$ | 2 μL |
| 10 mM dNTP mix | 1 μL |
| 100 mM DTT | 2 μL |
| total volume | 7 μL |

Add 7 μL of the above mixture to each of the sample tubes.

Mix and centrifuge briefly.

Incubate at room temperature for 5 minutes.

Add 1 μL of Superscript II RT to each sample tube.

Mix and centrifuge briefly.

Incubate at room temperature for 10 minutes.

Transfer tubes to 42° C. and incubate for 50 minutes.

Terminate the reactions by incubating at 70° C. for 15 minutes.

Chill on ice for at least 2 minutes and centrifuge briefly.

C. PCR Amplification

Prepare a master mix with the following materials and amounts in the order indicated. Prepare enough of the mix for one extra reaction. Keep the master mix on ice.

| Component | Volume per reaction |
|---|---|
| 5' Primer (100 ng/μL) | 0.4 μL |
| 3' Primer (100 ng/μL) | 0.4 μL |
| 10 × PCR Buffer | 2.5 μL |
| 25 mM $MgCl_2$ | 1.5 μL |
| 2.5 mM dNTP mix | 2.0 μL |
| Amplitaq Gold | 0.25 μL |
| purified water | 15.95 μL |
| total volume | 23 μL |

For each sample or cDNA control, add 23 μL of the above mixture to a thin walled, PCR tube.

To each PCR tube, add 2 μL of sample or control cDNA from the first strand reaction. Keep all PCR tubes on ice.

Perform PCR using the following cycle:

| Step | Process | Time (min.) | Temp. (° C.) |
|---|---|---|---|
| Hold 1 | Denaturation | 10 | 96 |
| 2 | Denaturation | 0.5 (30 sec.) | 96 |
| 3 | Annealing | 1 | 55 |
| 4 | Extension | 2 | 72 |
| | Repeat steps 2–4 for total of 35 cycles (see note) | | |
| Hold 2 | Long Extension | 7 | 72 |
| Hold 3 | Chill and Hold | hold | 4 |

Note: The optimal number of cycles will have to be determined dependent on band intensity.

Run 10 $\mu$L of the product on a 2% TAE agarose gel with a 1 kb ladder as a marker.

The present invention provides novel materials and methods for the diagnosis and treatment of endometriosis. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A method for use in the diagnosis of endometriosis in a subject comprising the steps of:

detecting a test amount of a prothymosin gene product in a sample from the subject; and comparing the test amount with a normal amount of the prothymosin gene product in a control sample, whereby a test amount above the normal amount provides a positive indication in the diagnosis of endometriosis.

2. The method of claim 1 wherein the sample comprises ectopic endometrial tissue, eutopic endometrial tissue, peritoneal fluid, blood, vaginal secretion or urine.

3. The method of claim 1 wherein the prothymosin gene product is prothymosin mRNA or cDNA.

4. The method of claim 3 wherein the step of detecting comprises the steps of:

contacting the prothymosin mRNA or cDNA with a polynucleotide of at least 7 to about 50 nucleotides in length that specifically hybridizes to the prothymosin mRNA or cDNA and detecting hybridization between the polynucleotide and the mRNA or cDNA.

5. The method of claim 4 wherein the polynucleotide comprises DNA or RNA.

6. The method of claim 4 wherein the polynucleotide comprises a nucleotide analog selected from the group consisting of phosphorothioates, phosphoramidates, methyl phosphonates, chiral-methyl phosphonates, 2-O-methyl ribonucleotides, and peptide-nucleic acids.

7. The method of claim 4 wherein the polynucleotide comprises a detectable moiety, and the step of detecting hybridization comprises detecting the moiety.

8. The method of claim 4 wherein the polynucleotide is a primer and the step of detecting hybridization comprises:

initiating reverse transcription of prothymosin mRNA with the primer, and detecting a prothymosin mRNA reverse transcript;

whereby detection of the reverse transcript indicates that the polynucleotide has specifically hybridized to prothymosin mRNA.

9. The method of claim 4 wherein the prothymosin mRNA or cDNA is immobilized and the step of contacting comprises contacting the immobilized mRNA or cDNA with the polynucleotide.

10. The method of claim 4 wherein the polynucleotide is immobilized and the step of contacting comprises contacting the immobilized polynucleotide with the prothymosin mRNA or cDNA.

11. The method of claim 7 wherein the detectable moiety is a fluorescent label, a radioactive label, an enzymatic label, a biotinyl group, or an epitope recognized by a secondary reporter.

12. The method of claim 9 wherein the biological sample is a fixed tissue sample and the step of contacting comprises contacting the polynucleotide with the mRNA or cDNA in situ on the fixed tissue sample.

13. The method of claim 10 wherein the immobilized polynucleotide is comprised within a polynucleotide array.

14. The method of claim 3 wherein the step of detecting comprises the steps of:

amplifying the prothymosin mRNA or cDNA to produce an amplification product and detecting the amplification product.

15. The method of claim 14 wherein the step of detecting the amplification product comprises:

contacting the amplification product with a polynucleotide of at least 7 to about 50 nucleotides in length that specifically hybridizes to the amplification product, and detecting hybridization between the polynucleotide and the amplification product.

16. The method of claim 14 wherein the step of detecting the amplification product comprises determining the nucleotide sequence of the amplification product.

17. The method of claim 14 wherein the step of detecting the amplification product comprises determining the mass of the amplification product.

18. The method of claim 15 wherein the polynucleotide comprises DNA or RNA.

19. The method of claim 15 wherein the polynucleotide comprises a nucleotide analog selected from the group consisting of phosphorothioates, phosphoramidates, methyl phosphonates, chiral-methyl phosphonates, 2-O-methyl ribonucleotides, and peptide-nucleic acids.

20. The method of claim 15 wherein the polynucleotide comprises a detectable moiety, and the step of detecting hybridization comprises detecting the moiety.

21. The method of claim 20 wherein the detectable moiety is a fluorescent label, a radioactive label, an enzymatic label, a biotinyl group, or an epitope recognized by a secondary reporter.

22. The method of claim 1 wherein the prothymosin gene product is prothymosin polypeptide.

23. The method of claim 22 wherein the step of detecting comprises detecting prothymosin polypeptide by immunoassay.

24. The method of claim 22 wherein the step of detecting comprises contacting the sample with an affinity agent that binds to prothymosin polypeptide and detecting binding between the affinity agent and the prothymosin polypeptide.

25. The method of claim 22 wherein the step of detecting comprises detecting an analyte in the sample having the mass of prothymosin polypeptide.

26. The method of claim 23 wherein the immunoassay is non-competitive immunoassay.

27. The method of claim 23 wherein the immunoassay is competitive immunoassay.

28. The method of claim 23 wherein the immunoassay comprises detecting binding between the prothymosin polypeptide and an antibody comprising a detectable moiety selected from the group consisting of a fluorescent label, a radioactive label, an enzymatic label, a biotinyl group, and an epitope recognized by a secondary reporter.

29. The method of claim 24 wherein the step of detecting binding comprises detecting bound prothymosin polypeptide by mass spectrometry.

30. The method of claim 26 wherein the non-competitive immunoassay comprises the steps of:

capturing the prothymosin polypeptide from the sample on a solid phase with a first antibody specific for prothymosin polypeptide; and detecting capture of the prothymosin polypeptide by contacting the solid phase with a second antibody specific for prothymosin polypeptide and detecting binding between the second antibody and prothymosin polypeptide.

31. The method of claim 26 wherein the non-competitive immunoassay comprises the steps of:

binding the prothymosin polypeptide from the sample to a solid phase; and detecting the prothymosin polypeptide by contacting the solid phase with an antibody specific for prothymosin polypeptide and detecting binding between the antibody and prothymosin polypeptide.

32. A method for use in the monitoring the progress of endometriosis in a subject comprising the steps of:

detecting a first test amount of a prothymosin gene product in a sample from the subject at a first time;

detecting a second test amount of the prothymosin gene product in a sample from the subject at a second, later time; and comparing the first test amount with the second test amount, whereby an increase in the amount between the first time and the second time indicates progression of endometriosis and a decrease in the amount between the first time and the second time indicates remission of endometriosis.

* * * * *

SEQUENCE LISTING

```
<160> NUMBER OF SEQ ID NOS: 4

<210> SEQ ID NO 1
<211> LENGTH: 1161
<212> TYPE: DNA
<213> ORGANISM: Homo sapiens
<220> FEATURE:
<223> OTHER INFORMATION: prothymosin clone REPRO-EN-203
<221> NAME/KEY: CDS
<222> LOCATION: (166)..(498)
<223> OTHER INFORMATION: prothymosin deduced amino acid sequence

<400> SEQUENCE: 1

gaaaagccat ctttgcattg ttcctcatcc gcctccttgc tcgccgcagc cgcctccgcc      60

gcgcgcctcc tccgccgccg cggactccgg cagctttatc gccagagtcc ctgaactctc     120

gctttctttt taatcccctg catcggatca ccggcgtgcc ccacc atg tca gac gca     177
                                                  Met Ser Asp Ala
                                                    1

gcc gta gac acc agc tcc gaa atc acc acc aag gac tta aag gag aag       225
Ala Val Asp Thr Ser Ser Glu Ile Thr Thr Lys Asp Leu Lys Glu Lys
  5                  10                  15                  20

aag gaa gtt gtg gaa gag gca gaa aat gga aga gac gcc cct gct aac       273
Lys Glu Val Val Glu Glu Ala Glu Asn Gly Arg Asp Ala Pro Ala Asn
                25                  30                  35

ggg aat gct aat gag gaa aat ggg gag cag gag gct gac aat gag gta       321
Gly Asn Ala Asn Glu Glu Asn Gly Glu Gln Glu Ala Asp Asn Glu Val
            40                  45                  50

gac gaa gaa gag gaa gaa ggt ggg gag gaa gag gag gag gaa gaa gaa       369
Asp Glu Glu Glu Glu Glu Gly Gly Glu Glu Glu Glu Glu Glu Glu Glu
        55                  60                  65

ggt gat ggt gag gaa gag gat gga gat gaa gat gag gaa gct gag tca       417
Gly Asp Gly Glu Glu Glu Asp Gly Asp Glu Asp Glu Glu Ala Glu Ser
    70                  75                  80

gct acg ggc aag cgg gca gct gaa gat gat gag gat gac gat gtc gat       465
Ala Thr Gly Lys Arg Ala Ala Glu Asp Asp Glu Asp Asp Asp Val Asp
 85                  90                  95                 100

acc aag aag cag aag acc gac gag gat gac tagacagcaa aaaaggaaaa         515
Thr Lys Lys Gln Lys Thr Asp Glu Asp Asp
               105                 110

gttaaactaa aaaaaaaaag gccgccgtga cctattcacc ctccacttcc cgtctcagaa     575
```

-continued

```
tctaaacgtg gtcaccttcg agtagagagg cccgcccgcc caccgtgggc agtgccaccc    635

gcagatgaca cgcgctctcc accacccaac ccaaaccatg agaatttgca acaggggagg    695

aaaaaagaac caaaacttcc aaggccctgc tttttttctt aaaagtactt taaaaaggaa    755

atttgtttgt atttttttatt tacattttat atttttgtac atattgttag ggtcagccat    815

ttttaatgat ctcggatgac caaaccagcc ttcggagcgt tctctgtcct acttctgact    875

ttacttgtgg tgtgaccatg ttcattataa tctcaaagga gaaaaaaaac cttgtaaaaa    935

aagcaaaaat gacaacagaa aaacaatctt attccgagca ttccagtaac ttttttgtgt    995

atgtacttag ctgtactata agtagttggt ttgtatgaga tggttaaaaa ggccaaagat   1055

aaaaggtttc tttttttttc ctttttgtc tatgaagttg ctgtttattt tttttggcct   1115

gtttgatgta tgtgtgaaac aatgttgtcc aacaataaac aggaat                  1161


<210> SEQ ID NO 2
<211> LENGTH: 110
<212> TYPE: PRT
<213> ORGANISM: Homo sapiens

<400> SEQUENCE: 2

Met Ser Asp Ala Ala Val Asp Thr Ser Ser Glu Ile Thr Thr Lys Asp
  1               5                  10                  15

Leu Lys Glu Lys Lys Glu Val Val Glu Glu Ala Glu Asn Gly Arg Asp
             20                  25                  30

Ala Pro Ala Asn Gly Asn Ala Asn Glu Glu Asn Gly Glu Gln Glu Ala
         35                  40                  45

Asp Asn Glu Val Asp Glu Glu Glu Glu Glu Gly Gly Glu Glu Glu Glu
     50                  55                  60

Glu Glu Glu Glu Gly Asp Gly Glu Glu Glu Asp Gly Asp Glu Asp Glu
 65                  70                  75                  80

Glu Ala Glu Ser Ala Thr Gly Lys Arg Ala Ala Glu Asp Asp Glu Asp
                 85                  90                  95

Asp Asp Val Asp Thr Lys Lys Gln Lys Thr Asp Glu Asp Asp
            100                 105                 110


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:5' primer

<400> SEQUENCE: 3

ctgacaatga ggtagacgaa g                                               21


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:3' primer

<400> SEQUENCE: 4

agtaaagtca gaagtaggac                                                 20
```